United States Patent [19]

Andre et al.

[11] Patent Number: 5,679,690

[45] Date of Patent: Oct. 21, 1997

[54] CONCENTRATED AQUEOUS SOLUTIONS OF ARGATROBAN

[75] Inventors: Frédéric Andre, Antony; Véronique Avril, Paris; Jean Montel, Chatou, all of France

[73] Assignee: Synthelabo, Le Plessis Robinson, France

[21] Appl. No.: 382,791

[22] Filed: Feb. 2, 1995

[30] Foreign Application Priority Data

Feb. 3, 1994 [FR] France .................... 94 01195

[51] Int. Cl.$^6$ .................... A61K 31/47; C07D 401/12
[52] U.S. Cl. .................... 514/314; 552/550
[58] Field of Search .................... 514/314; 546/166; 552/550

[56] References Cited

FOREIGN PATENT DOCUMENTS

| 0 008 746 | 3/1980 | European Pat. Off. . |
|---|---|---|
| 0 301 970 | 2/1989 | European Pat. Off. . |
| 0 565 897 | 10/1993 | European Pat. Off. . |
| 0565897 | 10/1993 | European Pat. Off. . |

OTHER PUBLICATIONS

Hawley, G.G., The Condensed Chemical Dictionary, 1981, Van Norstrand Reinhold Co., pp. 266, 409, and 694.

Holum, J.R., Elements of General and Biological Chemistry, 8th ed., John Wiley & Sons Inc., 1991, pp. 303, 310–313.

*Primary Examiner*—Bernard Dentz
*Assistant Examiner*—Garth M. Dahlen
*Attorney, Agent, or Firm*—Jacobson, Price, Holman & Stern, PLLC

[57] ABSTRACT

Concentrated aqueous solutions of argatroban containing argatroban, a micelle-forming agent and a lipoid substance.

10 Claims, No Drawings

CONCENTRATED AQUEOUS SOLUTIONS OF ARGATROBAN

The present invention relates to a new pharmaceutical formulation for argatroban.

Argatroban, a synthetic thrombin inhibitor, is a compound which is sparingly soluble in water (about 1 mg/ml). Required doses in certain therapeutic indications necessitate, therefore, the administration of several hundred milliliters per day when argatroban is in the form of a mere aqueous solution.

It is known that certain agents can be used to enable an increase in the concentration of solutions and limit the volumes administered. For example, studies have been performed of the potential use of small quantities of ethanol, propylene glycol, polyethylene glycol, surface-active agents such as sorbitan esters or polyoxyethylated derivatives of castor oil. Some of these agents have enabled an increase in argatroban solubility. However, major problems of local tolerance and/or general reactions of the anaphylactic type have arisen with all resulting solutions.

According to the present invention there is provided a new pharmaceutical formulation for argatroban which improves its solubility in water by the adaptation of the mixed micelle technique.

This formulation is a concentrated aqueous solution of argatroban, which comprises argatroban, one or more micelle-forming agents and one or more lipoid substance such as phosphatides.

It may also optionally contain one or more additives or excipients usually used in the preparation of liquid pharmaceutical forms, such as osmolarity agents, buffer agents, antioxidants and preservatives, or the additives required for the preparation of a dried form (obtained by freeze-drying, nebulization, atomization, etc.) from which may be obtained, after reconstitution, the liquid form.

Suitable micelle-forming agents include, for example, cholic acid derivatives of general formula

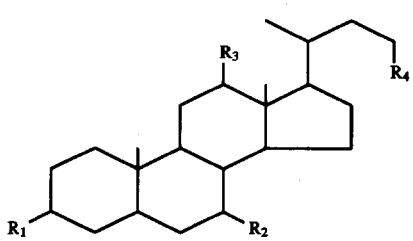

in which each of $R_1$, $R_2$ and $R_3$ independently represents a hydrogen atom, hydroxy or keto exocyclic group and $R_4$ represents a carboxy group or a carboxy group bonded by an amide linkage to the amino group of an amino acid, which may contain one or two double bonds in the steroid skeleton, for example in positions 7–8, 11–12 or 9–11.

More preferably, compounds of the formula (I) are used in which $R_1$, $R_2$, $R_3$ and $R_4$ have the following values: $R_1$, $R_2$ and $R_3$=OH, $R_4$=COOH; $R_1$, $R_2$ and $R_3$=OH, $R_4$=CONH=CH$_2$—COOH; $R_1$, $R_2$ and $R_3$=OH, $R_4$=CONH—CH$_2$—CH$_2$—SO$_3$H; $R_1$ and $R_3$=OH, $R_2$=H, $R_4$=COOH; $R_1$ and $R_3$=OH, $R_2$=H, $R_4$=CONH—CH$_2$—COOH; $R_1$ and $R_3$=OH, $R_2$=H, $R_4$=CONH—CH$_2$—CH$_2$—SO$_3$H; $R_1$ and $R_2$=OH, $R_3$=H, $R_4$=COOH; $R_1$ and $R_2$=OH, $R_3$=H, $R_4$=CONH—CH$_2$—COOH; $R_1$ and $R_2$=OH, $R_3$=H, $R_4$=CONH=CH$_2$—CH$_2$—SO$_3$H.

The compounds of formula (I) are optionally used in the form of salts, preferably alkali metal salts, and more preferably sodium salts.

As lipoid substances, the following compounds are preferably used: phosphatidylcholines, phosphatidylethanolamine, phosphatidylinositol, phosphatidylserines, diphosphatidylglycerol, glycerine ether-phosphatides, plasmalogens, sphingomyelin, sulphatides and monoglycerides. The more preferred lipoid substances are phosphatides, and phosphatidylcholines are used most preferably.

The micelle-forming agent may be optionally a mixture of two or more cholic acid derivatives. A mixture of two or more lipoid substances may also optionally be used.

The molar ratio between the lipoid component (pure compound or mixture) and the micelle-forming component (pure compound or mixture) is preferably from 0.1/1 to 2/1, more preferably from 0.5/1 to 1.5/1.

The final micelle-forming agent concentration in the pharmaceutical formulation according to the invention, variable as a function of the desired argatroban concentration, is generally from 0.01 to 0.5M.

Argatroban solutions according to the invention may be prepared using the following methods:

1. Dissolution of all the components in water, with vigorous stirring.

2. Dissolution of the mixed micelle components in a dilute organic solvent, then evaporation of the solvent, taking-up of the residue in water, to which the other excipients necessary to adjust the pH, the osmolarity and/or necessary to the stability of the solution have optionally been added as required, and finally incorporation of argatroban with stirring.

3. Dissolution of argatroban and micelle components in an organic solvent, then evaporation of the solvent and taking-up of the residue in water to which the other excipients as described in 2 have optionally been added as required.

The solutions thus obtained have an argatroban concentration higher than 1 mg/ml and, more specifically, from 1 mg/ml to 21 mg/ml.

To a solution obtained by one of the methods described above it is possible to add one or more substances such as monosaccharides, oligosaccharides, polyalcohols, amino acids, polymers such as polyvinylpyrrolidone, gelatin, dextran, albumin, etc., at concentrations from 0.1 to 20%. The preparation is optionally then dried by atomization or by lyophilization. The solid material thus obtained, which should be kept in a sealed container under a controlled atmosphere, can be solubilized at the time of use by addition of an appropriate solvent, such as water for injectable preparations.

A clear solution is thus obtained which has a concentration of argatroban of higher than 1 mg/ml, preferably from 1 to 21 mg/ml.

The following examples illustrate the present invention:

EXAMPLE 1

1.2 g of purified egg lecithin, 0.7 g of sodium glycocholate and 0.125 g of argatroban are dissolved in 75 mg of 95% ethanol with magnetic stirring. The ethanol is then evaporated under reduced pressure and the residue is taken up with stirring at room temperature in 25 ml of 0.06M phosphate buffer (pH=6). A clear solution is obtained, with a concentration of 5 mg/ml.

This solution, stored at +4° C., remains stable for several weeks.

EXAMPLE 2

0.750 g of purified egg lecithin and 0.490 g of sodium glycocholate are dissolved in 10 ml of 95% ethanol. After evaporation of the solvent under reduced pressure, the residue is dissolved in 15 ml of 0.06M phosphate buffer (pH=6) and 0.100 g of argatroban is added with vigorous stirring. Stirring is maintained for several hours under bubbled nitrogen and then the volume is adjusted to 20 ml by addition of phosphate buffer. A solution is obtained with a concentration of 5 mg/ml.

EXAMPLE 3

According to the procedure in Example 2, a solution is prepared containing 0.1M sodium glycocholate and 0.1M phosphatidyl choline, then an excess of argatroban is added, and the solution is stirred for 48 hours and filtered through a 0.22 μm-meshed membrane. A solution is obtained with a concentration of 11.3 mg/ml.

EXAMPLE 4

According to the procedure in Example 3, using a solution containing 0.075M sodium glycocholate, a solution is obtained with a concentration of 9 mg/ml.

EXAMPLE 5

According to the procedure in Example 3, using a solution containing 0.15M sodium glycocholate and 0.15M phosphatidylcholine, a solution is obtained with a concentration of 16.9 mg/ml.

EXAMPLE 6

According to the procedure in Example 3, using a solution containing 0.15M phosphatidylcholine and 0.15M sodium taurocholate, a solution is obtained with a concentration of 13 mg/ml.

EXAMPLE 7

According to the procedure in Example 3, using 0.15M of a mixture containing 65% sodium taurocholate and 35% sodium glycocholate and 0.15M phosphatidylcholine, a solution is obtained with a concentration of 20.6 mg/ml.

EXAMPLE 8

According to the procedure in Example 3, using 0.15M sodium taurocholate and 0.15M of a mixture of phosphatidylcholine and phosphatidylethanolamine (at a ratio of 8.5/1), a solution is obtained with a concentration of 20.1 mg/ml.

Argatroban solutions according to the invention may be administered via the parenteral, oral, nasal, ocular or retroocular routes.

We claim:

1. A concentrated aqueous solution of argatroban, which comprises argatroban, one or more micelle-forming agents and one or more lipoid substances, wherein the micelle-forming agent is a cholic acid derivative of general formula:

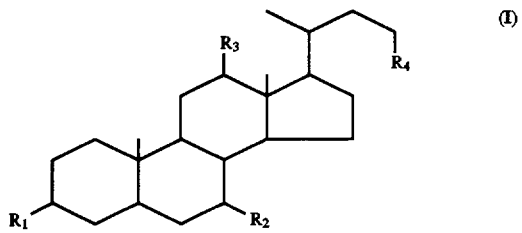

in which each of $R_1$, $R_2$ and $R_3$ independently represents a hydrogen atom, hydroxy group or keto exocyclic group, and $R_4$ represents a carboxy group or a carboxy group bonded by an amide linkage to the amino group of an amino acid.

2. A solution according to claim 1 wherein the derivative of general formula (I) contains one or two double bonds in the steroid skeleton.

3. A solution according to claim 1, wherein the derivative of general formula (I) is in the form of an alkali metal salt.

4. A solution according to claim 1, wherein the lipoid substance is a phosphatide.

5. A solution according to claim 4, wherein the phosphatide is a phosphatidylcholine.

6. A solution according to claim 1, which contains one or more excipients as usually used in the preparation of liquid pharmaceutical forms or of dried pharmaceutical forms which lead after reconstitution to liquid forms.

7. A solution according to claim 1, wherein the molar ratio between the lipoid substance and the micelle-forming agent is from 0.1/1 to 2/1.

8. A solution according to claim 1, wherein the concentration of micelle-forming agent is from 0.01 to 0.5M.

9. A solution according to claim 1, wherein the argatroban concentration is from 1 mg/ml to 21 mg/ml.

10. A solution prepared at the time of use by dissolving a solid material obtained by atomization or lyophilization of all or part of the components of a solution according to claim 1.

* * * * *